(12) United States Patent
Ishii et al.

(10) Patent No.: US 8,426,645 B2
(45) Date of Patent: Apr. 23, 2013

(54) PROCESS FOR PRODUCTION OF OPTICALLY ACTIVE FLUOROAMINE

(75) Inventors: Akihiro Ishii, Kawagoe (JP); Takako Yamazaki, Kawagoe (JP); Manabu Yasumoto, Kawagoe (JP)

(73) Assignee: Central Glass Company, Limited, Ube-shi (JP)

( * ) Notice: Subject to any disclaimer, the term of this patent is extended or adjusted under 35 U.S.C. 154(b) by 125 days.

(21) Appl. No.: 12/919,162

(22) PCT Filed: Jan. 27, 2009

(86) PCT No.: PCT/JP2009/051232
§ 371 (c)(1),
(2), (4) Date: Aug. 24, 2010

(87) PCT Pub. No.: WO2009/116320
PCT Pub. Date: Sep. 24, 2009

(65) Prior Publication Data
US 2011/0034732 A1 Feb. 10, 2011

(30) Foreign Application Priority Data
Mar. 21, 2008 (JP) ................................. 2008-072919

(51) Int. Cl.
C07C 257/12 (2006.01)
C07D 263/04 (2006.01)

(52) U.S. Cl.
USPC .......................................... 564/278; 548/215

(58) Field of Classification Search .................. None
See application file for complete search history.

(56) References Cited

U.S. PATENT DOCUMENTS

| 4,528,028 A | 7/1985 | Flint et al. |
| 7,807,858 B2 * | 10/2010 | Ishii et al. ..................... 570/142 |
| 8,058,412 B2 * | 11/2011 | Ishii et al. .......................... 532/1 |
| 2002/0013499 A1 | 1/2002 | Onishi et al. |
| 2008/0125589 A1 | 5/2008 | Ishii et al. |
| 2009/0250658 A1 | 10/2009 | Ishii et al. |

FOREIGN PATENT DOCUMENTS

| JP | 2006-290870 A | 10/2006 |
| JP | 2008-7488 A | 1/2008 |
| WO | WO 00/44706 A1 | 8/2000 |
| WO | WO 2006/098444 A1 | 9/2006 |

OTHER PUBLICATIONS

Liu, H.-B.,Wang, M., Wang, Y., Gu, Q. Synthesis of 3-aryl-5-t-butylsalicyaldehydes and their chiral schiff base compounds. Synthetc Commun. 2007, 37, 3815-3826.*
Bey, P., Vevert, J.P. New approach to the synthesis of alpha-halogenomethyl-alpha-amino acids. Tetrahedron Lett. 1978, 9, 1215-1218.*
McMurry, John. Organic Chemistry. 5th ed. Pacific Grove: Brooks/Cole, 2000.*
Rac, B., Molnar, A., Forgo, P., Mohai, M., Bertoti, I. A comparative study of solid sulfonic acid catalysts based on various ordered mesoporous silica materials. J. Mol. Catal. A-Chem. 2006, 244, 46-57.*
International Search Report with English translation dated Apr. 7, 2009 (Four (4) pages).
PCT/ISA/237 (Three (3) pages), 2009.
Chengfeng Ye, et al, "Rearrangements accompanying fluorination of 2-amino alcohols and 1,2-diols with Deoxo-Fluor™", Journal of Fluorine Chemistry (Netherlands), 2004, vol. 125, p. 1869-1872.
Lila Somekh et al., "Facile Stereospecific Synthesis of Alpha-Fluoro-Beta-amino Acids", Journal of American Chemical Society (U.S.), 1982, vol. 104, p. 5836-5837.
John Wiley & Sons, Inc, "Protective Groups in Organic Synthesis", Third Edition, 1999, (Twenty-six (26) pages).
Chinese Office Action dated Nov. 5, 2012 (seven (7) pages).
Li et al., "Stereoselective Nucleophilic Monofluoromethylation of N-(tert-Butanesulfinyl)imines with Fluoromethyl Phenyl Sulfone", Organic Letters, 2006, vol. 8, No. 8, pp. 1693-1696 (four (4) sheets).
Berbasov et al., "Synthesis of highly 1,3-proton shift transferable N-benzyl imines of trifluoroacetophenone under the "low-basicity" reaction conditions", Journal of Fluorine Chemistry, 2004, vol. 125, pp. 603-607 (five (5) sheets).

* cited by examiner

Primary Examiner — Jason M Nolan
Assistant Examiner — Po-Chih Chen
(74) Attorney, Agent, or Firm — Crowell & Moring LLP

(57) ABSTRACT

Disclosed is a process for producing a protected optically active fluoroamine, which comprises the step of reacting an imine-protected optically active hydroxyamine, an oxazolidine-protected optically active hydroxyamine, or a mixture of the imine-protected optically active hydroxyamine and the oxazolidine-protected optically active hydroxyamine, with sulfuryl fluoride ($SO_2F_2$) in the presence of a tertiary amine having a carbon number of 7 to 18 (produced by substituting all of three hydrogen atoms in ammonia by alkyl groups). The desired optically active fluoroamine can be produced by hydrolyzing the protected optically active fluoroamine under acidic conditions.

9 Claims, No Drawings

PROCESS FOR PRODUCTION OF OPTICALLY ACTIVE FLUOROAMINE

TECHNICAL FIELD

The present invention relates to an industrial production process of an optically active fluoroamine, which is important as an intermediate of pharmaceutical and agrichemical products.

BACKGROUND ART

An optically active fluoroamine, which is the target of the present invention, is an important intermediate of pharmaceutical and agrichemical products. The direct production of the optically active fluoroamine is generally conducted by dehydroxyfluorination of a corresponding optically active amino alcohol in a protected amino form.

The present applicant has disclosed a process for producing an optically active fluoroamine by dehydroxyfluorination of an alcohol with the combined use of sulfuryl fluoride ($SO_2F_2$) and an organic base. This production process provides a target fluorinated compound (phthaloyl-protected form) with a yield of 23% in the case of using as a raw material an optically active amino alcohol of which the amino group (—$NH_2$) has been protected with a phthaloyl group (cf. Scheme 1: Patent Document 1).

Scheme 1

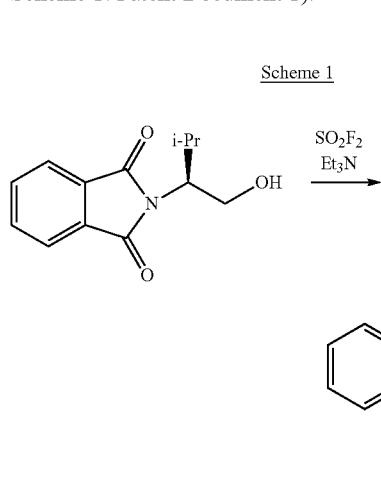

[Chem. 1]

i-Pr: isopropyl
Et: ethyl

Further, there is known a process for dehydroxyfluorination of an optically active amino alcohol in a protected amino form using a fluorination agent known as Deoxo-Fluor™ (cf. Scheme 2: Non-Patent Document 1) or DAST (cf. Scheme 3: Non-Patent Document 2).

Scheme 2

[Chem. 2]

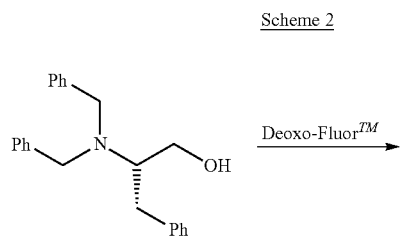

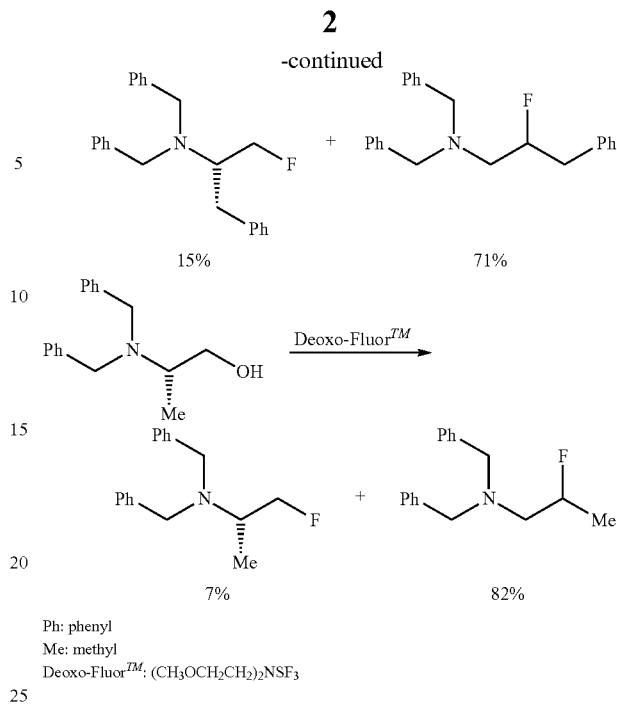

Ph: phenyl
Me: methyl
Deoxo-Fluor™: $(CH_3OCH_2CH_2)_2NSF_3$

Scheme 3

[Chem. 3]

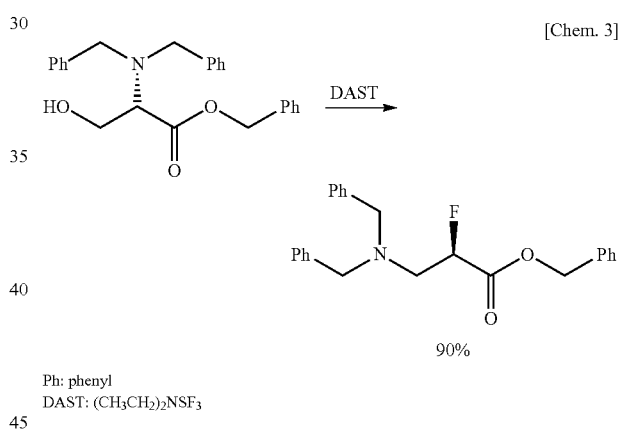

Ph: phenyl
DAST: $(CH_3CH_2)_2NSF_3$

Patent Document 1: International Publication No. 2006/098444 (Japanese Laid-Open Patent Publication No. 2006-290870)

Non-Patent Document 1: Journal of Fluorine Chemistry (Netherlands), 2004, Vol. 125, P.1869-1872

Non-Patent Document 2: Journal of American Chemical Society (US), 1982, Vol. 104, P.5836-5837

SUMMARY OF THE INVENTION

It is an object of the present invention to provide an industrial production process of an optically active fluoroamine.

It is known that the dehydroxyfluorination of the protected optically active amino alcohol involves neighboring-group participation of a nitrogen atom even when the amino group has been protected with a protecting group. For example, the dehydroxyfluorination reaction of a substrate having the same 1,2-amino alcohol structure as that in the present invention and containing a dibenzyl group as an amino protecting group cannot selectively produce a target compound with a fluorine atom simply substituted on its hydroxyl-bonded carbon atom and provides a rearranged form of the target compound as a main product (cf. Schemes 2 and 3).

The dehydroxyfluorination reaction of Patent Document 1, in which the phthaloyl-protected amino alcohol is dehydroxyfluorinated with sulfuryl fluoride, can limit neighboring-group participation of a nitrogen atom and produce the target compound by a relatively easy operation. The product yield is however merely 23% and is susceptible to improvement. Further, the reaction system is placed under basic conditions by the addition of hydrazine as a typical phthaloyl deprotecting agent. In such a basic reaction system, there occurs a side reaction between the deprotected amino group (nucleophilic moiety) and fluorine atom (electrophilic moiety) of the target compound. This results in a low deprotection yield without being able to prevent the target compound from intramolecular ring-closure to an aziridine, intermolecular polycondensation and hydrazine substitution etc. In view of the above facts that: the desired dehydroxyfluorination reaction does not proceed favorably under the disclosed reaction conditions; and the deprotection of the resultant fluorinated compound does not proceed selectively, it cannot always be said that the dehydroxyfluorination reaction of Patent Document 1 is practical for the production of the target optically active fluoroamine of the present invention.

Furthermore, the dehydroxyfluorination agents such as Deoxo-Fluor™ and DAST are expensive and have a danger of explosion whereby the use of these dehydroxyfluorination agents is limited to small-scale production purposes. There is thus a strong demand for a reaction agent that is not only capable of performing a desired dehydroxyfluorination reaction favorably but also suitable for large-scale production uses.

As described above, it has been demanded to develop a high-selectivity, high-yield production process suitable for mass production of an optically active fluoroamine of the after-mentioned formula [6]. In order to satisfy such a demand, it is important to find out an amino protecting group capable of preventing neighboring-group participation of the nitrogen atom effectively and enabling easy protection and deprotection of the amino group. It is also necessary to clarify reaction conditions under which the dehydroxyfluorination of the protected amino form proceeds favorably.

As a result of extensive researches made in view of the above problems, the present inventors have found that: the selection of an amino protecting group for an optically active hydroxyamine is important; and an imine-protected optically active hydroxyamine (hereinafter occasionally simply referred to as "imine form") of the present invention can be easily prepared by dehydrative condensation of an optically active hydroxyamine and an aldehyde and undergoes a desired dehydroxyfluorination reaction favorably with almost no side reaction such as rearrangement due to neighboring group participation of its nitrogen atom. The present inventors have also found that, although there is a difficulty in obtaining the imine form selectively by dehydrative condensation of the optically active hydroxyamine and the aldehyde, an oxazolidine-protected optically active hydroxyamine (hereinafter occasionally simply referred to as "oxazolidine form") generated as a by-product of the dehydrative condensation also serves as a suitable substrate in the dehydroxyfluorination reaction of the present invention (cf. Scheme 4).

Scheme 4

[Chem. 4]

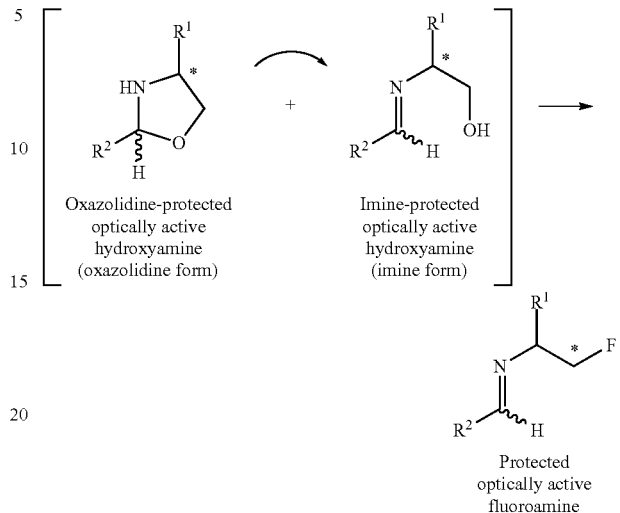

Oxazolidine-protected optically active hydroxyamine (oxazolidine form)

Imine-protected optically active hydroxyamine (imine form)

Protected optically active fluoroamine

The present inventors have further found that: the protected optically active fluoroamine obtained by the dehydroxyfluorination reaction can be easily deprotected by hydrolysis under acidic conditions; and, in contrast to the above-mentioned phthaloyl deprotection reaction under the basic conditions, the deprotection reaction under the acidic conditions makes it possible to limit nucleophilicity by protonation of the deprotected amino group and thus proceeds selectively with almost no side reaction.

For the above reasons, both of the imine form and the oxazolidine form are suitable protected amino forms in the present invention. In these protected amino forms, $R^2$ is particularly preferably an aromatic hydrocarbon group in view of the large-scale availability of the raw aldehyde material, the ease and selectivity of protection and deprotection of the amino group, the effect of preventing the reactivity of dehydroxyfluorination of the hydroxyamine and the neighboring-group participation of the nitrogen atom, the large-scale handling stability of various intermediates and the like.

On the other hand, the present inventors have found that: even if the suitable protected amino form, i.e., the imine form, oxazolidine form or mixture thereof is reacted with sulfuryl fluoride in the presence of triethylamine, which is heavily used as a typical organic base in Patent Document 1, the desired dehydroxyfluorination reaction does not proceed favorably; and the triethylamine nucleophilically attacks a fluorosulfuric acid ester intermediate in preference to the fluorine anion ($F^-$) so that there occurs a large amount of quaternary ammonium salt as a by-product (cf. Comparative Example 1; Scheme 5).

Scheme 5

[Chem. 5]

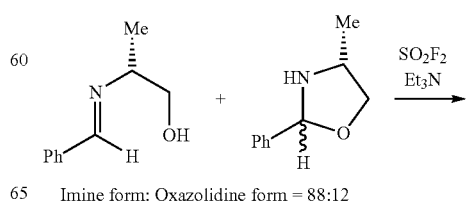

Imine form: Oxazolidine form = 88:12

-continued

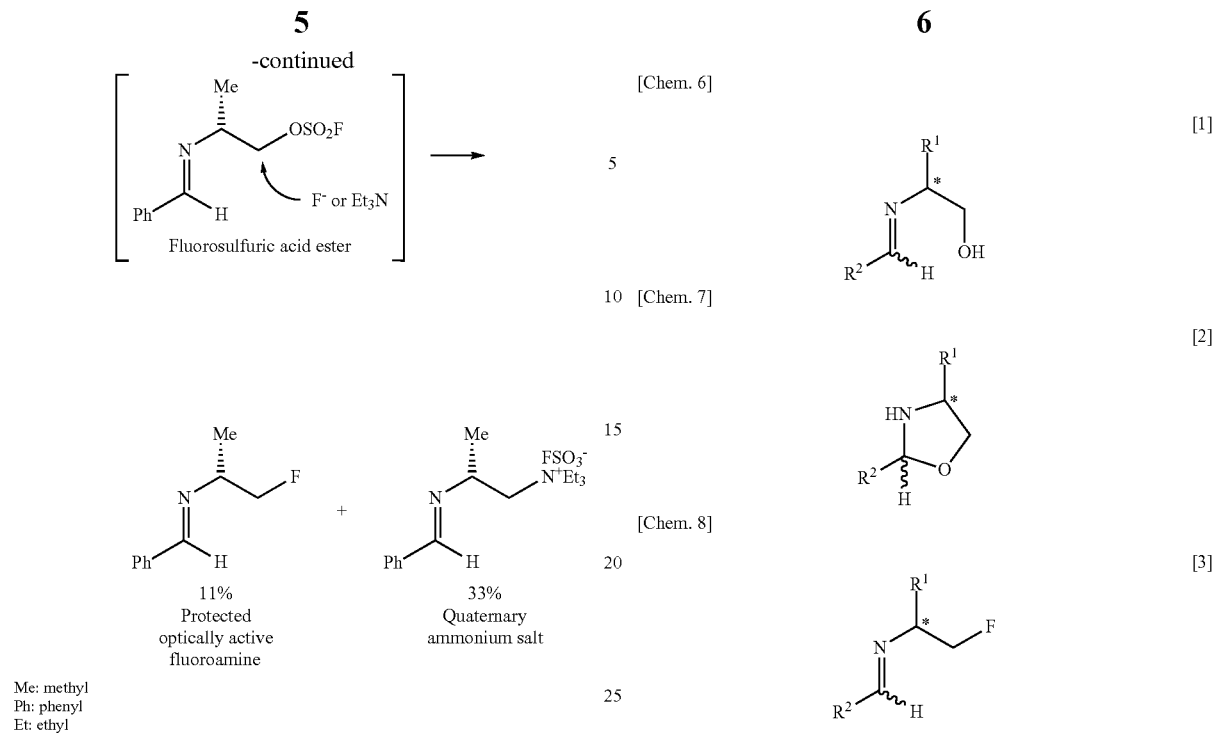

Me: methyl
Ph: phenyl
Et: ethyl

Under these circumstances, the present inventors have focused attention on the steric effect of an organic base and have found that the use of a tertiary amine having a carbon number of 7 to 18, preferably a tertiary amine having a carbon number of 8 to 12 and containing two or more alkyl groups of 3 or more carbon atoms (such as diisopropylethylamine, tri-n-butylamine etc.), as the organic base makes it possible to effectively prevent the generation of a quaternary ammonium salt as a by-product. The desired steric effect of the tertiary amine can be obtained sufficiently when the tertiary amine has a carbon number of up to 18. The carbon number of the tertiary amine is thus preferably up to 18, more preferably up to 12, in view of the large-scale availability of the amine, the productivity of the dehydroxyfluorination reaction system and the like.

Consequently, the present inventors have verified that it is important to use the suitable protected amino form in combination with the above specific tertiary amine for production of the target optically active fluoroamine of the present invention.

The present inventors have finally found a novel protected optically active fluoroamine as a useful key intermediate in the present invention.

As described above, the present inventors have found the particularly useful techniques for industrial production of the optically active fluoroamine. The present invention is based on these findings.

According to the present invention, there is provided a process (first process) for producing a protected optically active fluoroamine of the formula [3], comprising: reacting an imine-protected optically active hydroxyamine of the formula [1], an oxazolidine-protected optically active hydroxyamine of the formula [2] or a mixture thereof with sulfuryl fluoride ($SO_2F_2$) in the presence of a tertiary amine (in which all of three ammonia hydrogen atoms have been replaced by alkyl groups) having a carbon number of 7 to 18 where $R^1$ and $R^2$ each independently represent an alkyl group or an aromatic ring group: * represents an asymmetric carbon; the stereochemistry of the asymmetric carbon is maintained through the reaction; and the wavy line indicates in the formula (1) and in the formula (3) that the nitrogen-carbon double bond is in an E-configuration, a Z-configuration or a mixture thereof and indicates in the formula (2) that the substituent group $R^1$ is in a syn-configuration, an anti-configuration or a mixture thereof.

The first process may be a process (second process) for producing the protected optically active fluoroamine, in which: $R^2$ of the imine-protected optically active hydroxyamine of the formula [1] or the oxazolidine-protected optically active hydroxyamine of the formula [2] is an aromatic hydrocarbon group; and the tertiary amine has a carbon number of 8 to 12 and contains two or more alkyl groups of 3 or more carbon atoms.

The first or second process may be a process (third process) for producing the protected optically active fluoroamine, in which the imine-protected optically active hydroxyamine of the formula [1] or the oxazolidine-protected optically active hydroxyamine of the formula [2] is obtained by dehydrative condensation of an optically active hydroxyamine of the formula [4] and an aldehyde of the formula [5]

[Chem. 9]

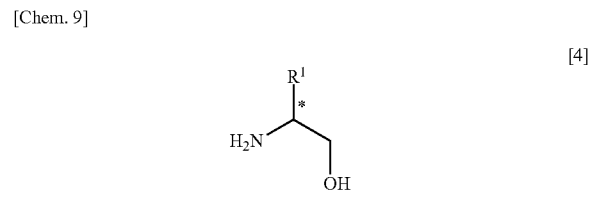

[Chem. 10]

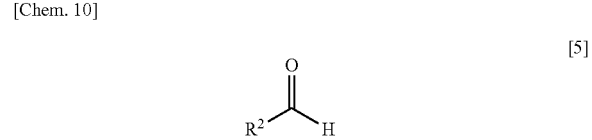

where $R^1$ and $R^2$ each independently represent an alkyl group or an aromatic ring group; and * represents an asymmetric carbon of which the stereochemistry is maintained through the dehydrative condensation.

There is also provided according to the present invention a process (fourth process) for producing an optically active fluoroamine of the formula [6], comprising: performing, under acidic conditions, hydrolysis of the protected optically active fluoroamine of the formula [3] produced by either one of the first to third processes

[Chem. 11]

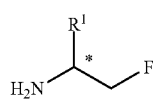

[6]

where $R^1$ represents an alkyl group or an aromatic ring group; and * represents an asymmetric carbon of which the stereochemistry is maintained through the hydrolysis.

There is further provided according to the present invention a protected optically active fluoroamine of the formula [3]

[Chem. 12]

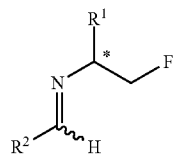

[3]

where $R^1$ and $R^2$ each independently represent an alkyl group or an aromatic ring group; * represents an asymmetric carbon; and the wavy line indicates that the nitrogen-carbon double bond is in an E-configuration, a Z-configuration or a mixture thereof.

In the formula [3], $R^2$ may be an aromatic hydrocarbon group.

DETAILED DESCRIPTION

The advantages of the present invention over the prior art technologies will be explained below.

The present invention is advantageous over Patent Document 1, in that it is possible in the present invention to improve the yield of the dehydroxyfluorination reaction significantly and to enable selective, high-yield deprotection of the resultant fluorinated compound.

The present invention is advantageous over Non-Patent Documents 1 and 2, in that it is possible in the present invention to limit the occurrence of a side reaction due to neighboring-group participation of the nitrogen atom and to adopt the dehydroxyfluorination agent suitable for large-scale production purposes. Sulfuryl fluoride used in the present invention has widely been applied as a fumigant and can easily be processed to an inorganic salt waste such as fluorite ($CaF_2$) or calcium sulfate.

All of the raw materials and reaction agents used in the present invention are available in large quantities and at relatively low cost. Further, the target compound can be produced with high chemical purity and high yield and with almost no by-product generation as all of the reaction steps are conducted under moderate reaction conditions. In addition, the stereochemistry of the asymmetric carbon can be maintained throughout the reaction steps so that the use of the raw material of higher optical purity leads to higher optical purity of the target compound.

The production process of the present invention is therefore industrially readily practicable and can solve all of the above-mentioned prior art problems.

The production process of the optically active fluoroamine according to the present invention will be described in detail below. In the present invention, the production process includes: a first step (dehydrative condensation reaction) for forming a protected optically active hydroxyamine of the formula [1] or [2] (imine form, oxazolidine form or mixture thereof) by dehydrative condensation of an optically active hydroxyamine of the formula [4] and an aldehyde of the formula [5]; a second step (dehydroxyfluorination reaction) for reacting the protected optically active hydroxyamine of the formula [1] or [2] (imine form, oxazolidine form or mixture thereof) with sulfuryl fluoride in the presence of a tertiary amine having a carbon number of 7 to 18, thereby converting the protected optically active hydroxyamine to a protected optically active fluoroamine of the formula [3]; and a third step (hydrolysis reaction) for forming an optically active fluoroamine of the formula [6] by hydrolysis of the protected optically active fluoroamine of the formula [3] under acidic conditions (cf. Scheme 6).

Scheme 6

[Chem. 13]

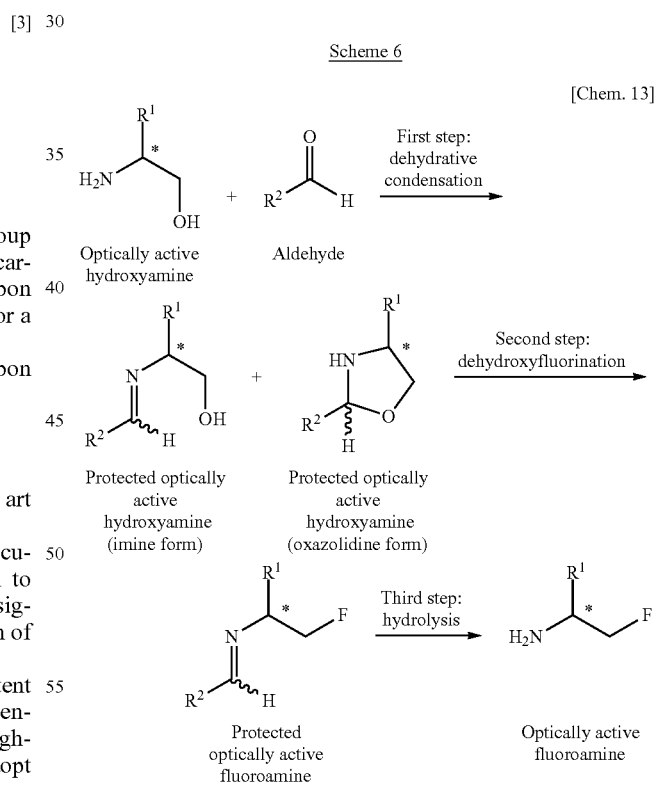

The first step (dehydrative condensation reaction) will be first explained in detail below.

In the optically active hydroxyamine of the formula [4], $R^1$ represents an alkyl group or an aromatic ring group. As the alkyl group, there can be used those having 1 to 18 carbon atoms and having a linear structure, a branched structure or a cyclic structure (in the case of 3 or more carbons). (The cyclic structure may be a monocyclic structure, a condensed polycyclic structure, a crosslinked structure, a spiro ring structure, a ring assembly structure or the like.) Any of the carbon atoms of the alkyl group may be replaced by any number of and any combination of hetero atoms such as nitrogen, oxygen and sulfur. (The nitrogen atom may have an alkyl group, an aromatic ring group, a protecting group or the like as a substituent; and the sulfur atom may have an oxygen atom as a substituent (—SO— or —$SO_2$—).) Two hydrogen atoms bonded to any (one) of the carbon atoms of the alkyl group may be replaced by any number of and any combination of nitrogen, oxygen and sulfur atoms. (In this case, the nitrogen, oxygen and/or sulfur atom forms an imino moiety, a carbonyl moiety or a thiocarbonyl moiety together with the carbon atom; and the nitrogen atom may have an alkyl group, an aromatic ring group, a protecting group or the like as a substituent.) Further, any adjacent two of the carbon atoms of the alkyl group may be replaced by any number of and any combination of unsaturated groups (double bond or triple bond). As the aromatic ring group, there can be used those having 1 to 18 carbon atoms, such as aromatic hydrocarbon groups, e.g., phenyl, naphthyl, anthryl etc. and aromatic heterocyclic groups containing heteroatoms such as nitrogen, oxygen and sulfur, e.g., pyrrolyl, furyl, thienyl, indolyl, benzofuryl, benzothienyl etc. (The nitrogen atom may have an alkyl group, an aromatic ring group, a protecting group or the like as a substituent; and the aromatic heterocyclic group may have a monocyclic structure, a condensed polycyclic structure, a ring assembly structure or the like.)

The alkyl group or aromatic ring group may have any number of and any combination of substituents on any of the carbon atoms thereof. Examples of the substituents are: halogen atoms such as fluorine, chlorine, bromine and iodine; azide group; nitro group; lower alkyl groups such as methyl, ethyl and propyl; lower haloalkyl groups such as fluoromethyl, chloromethyl and bromomethyl; lower alkoxy groups such as methoxy, ethoxy and propoxy; lower haloalkoxy groups such as fluoromethoxy, chloromethoxy and bromomethoxy; lower alkylamino groups such as dimethylamino, diethylamino and dipropylamino; lower alkylthio groups such as methylthio, ethylthio and propylthio; cyano group; lower alkoxycarbonyl groups such as methoxycarbonyl, ethoxycarbonyl and propoxycarbonyl; aminocarbonyl group ($CONH_2$); lower aminocarbonyl groups such as dimethylaminocarbonyl, diethylaminocarbonyl and dipropylaminocarbonyl; unsaturated groups such as alkenyl and alkynyl; aromatic ring groups such as phenyl, naphthyl, pyrrolyl, furyl and thienyl; aromatic ring oxy groups such as phenoxy, naphthoxy, pyrrolyloxy, furyloxy and thienyloxy; aliphatic heterocyclic groups such as piperidyl, piperidino and morpholinyl; protected hydroxyl groups; protected amino groups (including amino acids and peptide residues); protected thiol groups; protected aldehyde groups; protected carboxyl groups; and the like.

In the present specification, the following terms have the following meanings. The term "lower" means that the group to which the term is attached has 1 to 6 carbon atoms and has a linear structure, a branched structure or a cyclic structure (in the case of 3 carbons or more). It means that, when the "unsaturated group" is a double bond (alkenyl group), the double bond can be in an E-configuration, a Z-configuration or a mixture thereof. It means that the "protected hydroxyl, amino (including amino acid or peptide residue), thiol, aldehyde and carboxyl groups" may be those having protecting groups described in "Protective Groups in Organic Synthesis", Third Edition, 1999, John Wiley & Sons, Inc. and the like. (In this case, two or more functional groups may be protected with one protecting group.)

Further, the "unsaturated group", "aromatic ring group", "aromatic ring oxy group" and "aliphatic heterocyclic group" may be substituted with halogen atoms, azide group, nitro group, lower alkyl groups, lower haloalkyl groups, lower alkoxy groups, lower haloalkoxy groups, lower alkylamino groups, lower alkylthio groups, cyano group, lower alkoxycarbonyl groups, aminocarbonyl group, lower aminocarbonyl groups, protected hydroxyl groups, protected amino groups (including amino acids and peptide residues), protected thiol groups, protected aldehyde groups, protected carboxyl groups or the like.

Although the alkyl group or aromatic ring group is suitably used as $R^1$ in the optically active hydroxyamine of the formula [4], $R^1$ is preferably the alkyl group of 1 to 9 carbon atoms. The optically active hydroxyamine in which $R^1$ is the alkyl group of 1 to 9 carbon atoms is preferred in that: a raw material of the optically active hydroxyamine, i.e., an optically active α-amino acid is easily available on a large scale; and the optically active hydroxyamine can be easily prepared by reduction of the optically active α-amino acid. The optically active hydroxyamine in which R' is the alkyl group of 1 to 6 is commercially available in various forms and is thus particularly preferred as the starting material of the present invention.

In the optically active hydroxyamine of the formula [4], * represents an asymmetric carbon. The stereochemistry (absolute configuration and optical purity) of the asymmetric carbon is maintained through the dehydrative condensation reaction.

The absolute configuration of the asymmetric carbon can be either a R-configuration or a S-configuration and be set appropriately depending on the absolute configuration of the target optically active fluoroamine of the formula [6].

The optical purity of the asymmetric carbon can be indicated by enantiomer excess (ee). It suffices that the enantiomer excess is 80% ee or higher in view of the use of the target optically active fluoroamine of the formula [6] as a pharmaceutical/agrichemical intermediate. The enantiomer excess is generally preferably 90% ee or higher, more preferably 95% ee or higher.

In the aldehyde of the formula [5], $R^2$ represents an alkyl group or an aromatic ring group.

Examples of the alkyl group or aromatic ring group $R^2$ are the same as $R^1$ in the optically active hydroxyamine of the formula [4]. Among others, aromatic hydrocarbon groups are preferred. Particularly preferred are phenyl, substituted phenyl, naphthyl and substituted naphthyl. The aldehyde in which $R^2$ is phenyl, substituted phenyl, naphthyl or substituted naphthyl has the advantage of being industrially available at low cost in addition to the advantage of the use of the aromatic hydrocarbon group as $R^2$ described above in "Means for Solving the Problems".

It suffices to use the aldehyde of the formula [5] in an amount of 0.7 mol or more per 1 mol of the optically active hydroxyamine of the formula [4]. The amount of the aldehyde of the formula [5] used is generally preferably in the range of 0.8 to 5 mol, more preferably 0.9 to 3 mol, per 1 mole of the optically active hydroxyamine of the formula [4].

In the first step, the reaction is performed preferably in the presence of an acid catalyst or under dehydrative conditions. Depending on the combination of the raw substrate materials, the reaction may proceeds favorably even without the adoption of these reaction conditions.

Examples of the acid catalyst are: inorganic acids such as hydrogen chloride (hydrochloric acid), sulfuric acid, phosphoric acid, zinc chloride, titanium tetrachloride and tetraisopropoxy titanium; and organic acids such as benzenesulfonic acid, para-toluenesulfonic acid, pyridinium para-toluenesulfonate (PPTS) and 10-camphorsulfonic acid. Among others, sulfuric acid, para-toluenesulfonic acid and pyridinium para-toluenesulfonate (PPTS) are preferred. Particularly preferred are para-toluenesulfonic acid and pyridinium para-toluenesulfonate (PPTS). It suffices to use a catalytic amount of the acid catalyst per 1 mol of the optically active hydroxyamine of the formula [4]. The amount of the acid catalyst used is generally preferably in the range of 0.001 to 0.7 mol, more preferably 0.005 to 0.5 mol, per 1 mol of the optically active hydroxyamine of the formula [4].

Further, the reaction under the dehydrative conditions can be performed by using, as a reaction solvent, an aromatic hydrocarbon solvent that is inmiscible with water, lower in specific gravity than water and azeotropic with water, and refluxing the reaction system while removing by-product water with a Dean-Stark trap.

Examples of the reaction solvent are: aliphatic hydrocarbon solvents such as n-hexane, cyclohexane and n-heptane; aromatic hydrocarbon solvents such as benzene, toluene, ethylbenzene, xylene and mesitylene; halogenated hydrocarbon solvents such as methylene chloride, chloroform and 1,2-dichloroethane; ether solvents such as diethyl ether, tetrahydrofuran, diisopropyl ether and tert-butyl methyl ether; ester solvents such as ethyl acetate and n-butyl acetate; amide solvents such as N,N-dimethylformamide, N,N-dimethylacetoamide, N-methyl-pyrrolidone and 1,3-dimethyl-2-imidazolidinone; nitrile solvents such as acetonitrile and propionitrile; dimethyl sulfoxide; and the like.

Among others, n-hexane, n-heptane, toluene, xylene, mesitylene, methylene chloride, tetrahydrofuran, diisopropyl ether, tert-butyl methyl ether, ethyl acetate, N,N-dimethylformamide, N,N-dimethylacetoamide, acetonitrile, propionitrile and dimethyl sulfoxide are preferred. Particularly preferred are toluene, xylene, methylene chloride, tetrahydrofuran, diisopropyl ether, ethyl acetate, N,N-dimethylformamide and acetonitrile. These reaction solvents can be used alone or in combination thereof. Alternatively, the reaction may be performed in the absence of the reaction solvent in the first step.

It suffices to use the reaction solvent in an amount of 0.01 L (liter) or more per 1 mol of the optically active hydroxyamine of the formula [4]. The amount of the reaction solvent used is generally preferably in the range of 0.05 to 5 L, more preferably 0.1 to 3 L, per 1 mol of the optically active hydroxyamine of the formula [4].

Further, it suffices that the temperature condition ranges from −20 to +200° C. The temperature condition is generally preferably in the range of −10 to +175° C., more preferably 0 to +150° C.

The reaction time is generally 72 hours or less. As the reaction time depends on the combination of the raw substrate materials and the adopted reaction conditions, it is preferable to determine the time at which the raw substrate materials have almost disappeared as the end of the reaction while monitoring the progress of the reaction by any analytical means such as gas chromatography, thin-layer chromatography, liquid chromatography or nuclear magnetic resonance.

The target protected optically active hydroxyamine of the formula [1] or [2] can be obtained as the imine form, oxazolidine form or mixture thereof by ordinary post treatment of the reaction-terminated liquid. Herein, the nitrogen-carbon double bond of the imine form is in an E-configuration, a Z-configuration or a mixture thereof; and the oxazolidine form is in a syn-configuration, an anti-configuration or a mixture thereof with respect to the substituent group $R^1$. Although the ratio of these isomers depends on the combination of the raw substrate materials and the adopted reaction conditions, the dehydroxyfluorination reaction of the second step proceeds favorably without the influence of such an isomer ratio. Further, the target compound can be purified to a high chemical purity, as needed, by purification operation such as activated carbon treatment, distillation, recrystallization or column chromatography.

In the first step, the reaction proceeds favorably with high selectivity. It is thus possible to obtain the target compound of sufficient quality as the raw substrate material for the dehydroxyfluorination reaction of the second step only by evaporating the reaction solvent for removal of the by-product water. Such simple post treatment is suitable in view of industrial production uses. Next, the second step (dehydroxyfluorination reaction) will be explained in detail below.

It suffices to use the sulfuryl fluoride ($SO_2F_2$) in an amount of 0.7 mol or more per 1 mol of the protected optically active hydroxyamine of the formula [1] or [2] (imine form, oxazolidine form or mixture thereof). The amount of the sulfuryl fluoride used is generally preferably in the range of 0.8 to 10 mol, more preferably 0.9 to 5 mole, per 1 mol of the protected optically active hydroxyamine derivative of the formula [1] or [2].

In the second step, trifluoromethanesulfonyl fluoride ($CF_3SO_2F$) or perfluorobutanesulfonyl fluoride ($C_4F_9SO_2F$) may alternatively be used as the dehydroxyfluorination agent. There is however no particular advantage to using these reaction agents in view of their large-scale availability, waste disposal and the like.

As already explained above, it is important in the second step to perform the reaction in the presence of the tertiary amine of carbon number 7 to 18. In the present specification, the term "carbon number" refers to a total number of carbons of three alkyl groups; and the term "tertiary amine" refers to an amine in which all of three hydrogen atoms of ammonia have been replaced by alkyl groups. The tertiary amine of carbon number 7 to 18 has alkyl groups, each of which is either linear, branched or cyclic (in the case of 3 carbons or more). It is particularly preferable that the tertiary amine has a carbon number of 8 to 12 and contains two or more alkyl groups of 3 or more carbon atoms.

Preferred examples of the tertiary amine are: diisopropylethylamine (having a carbon number of 8 and containing two alkyl groups of 3 or more carbon atoms); tri-n-propylamine (having a carbon number of 9 and containing three alkyl groups of 3 or more carbon atoms); diisopropylisobutylamine (having a carbon number of 10 and containing three alkyl groups of 3 or more carbon atoms); di-n-butylisopropylamine (having a carbon number of 11 and containing three alkyl groups of 3 or more carbon atoms); tri-n-butylamine (having a carbon number of 12 and containing three alkyl groups of 3 or more carbon atoms); and the like. Among others, diisopropylethylamine and tri-n-butylamine are preferred. Particularly preferred is diisopropylethylamine. The tertiary amine is suitable for industrial production uses as it has high lipophilicity and thus can be easily recovered and recycled without reactivity deterioration.

It suffices to use the tertiary amine of carbon number 7 to 18 in an amount of 0.7 mol or more per 1 mol of the protected optically active hydroxyamine of the formula [1] or [2] (imine form, oxazolidine form or mixture thereof). The amount of the tertiary amine used is generally preferably in the range of 0.8 to 10 mol, more preferably 0.9 to 5 mol, per 1 mole of the protected optically active hydroxyamine of the formula [1] or [2].

In the second step, the reaction may be performed in the presence of "a salt or complex of a tertiary amine having a carbon number of 7 to 18 and hydrogen fluoride". However, the reaction proceeds favorably even in the absence of such a salt or complex. There is thus no need to perform the reaction in the presence of the salt or complex.

The same reaction solvent as that in the first step (dehydrative condensation reaction) can be used in the second step. Preferred examples and particularly preferred examples of the reaction solvent in the second step are also the same as those in the first step. The reaction solvents can be used alone or in combination thereof. Alternatively, the reaction may be performed in the absence of the reaction solvent in the second step.

It suffices to use the reaction solvent in an amount of 0.1 L (liter) or more per 1 mol of the protected optically active hydroxyamine of the formula [1] or [2] (imine form, oxazolidine form or mixture thereof). The amount of the reaction solvent used is generally preferably in the range of 0.2 to 10 L, more preferably 0.3 to 5 L, per 1 mol of the protected optically active hydroxyamine of the formula [1] or [2].

It suffices that the temperature condition ranges from −100 to +100° C. The temperature condition is generally preferably in the range of −50 to +50° C., more preferably −40 to +40° C. In the case where the temperature condition is set to be higher than or equal to a boiling point (−49.7° C.) of the sulfuryl fluoride, the reaction can be conducted using a pressure-proof reaction vessel.

It suffices that the pressure condition ranges from atmospheric pressure to 2 MPa. The pressure condition is generally preferably in the range of atmospheric pressure to 1.5 MPa, more preferably atmospheric pressure to 1 MPa. It is thus preferable to conduct the reaction using a pressure-proof reaction vessel made of a stainless steel (SUS) material, a glass (glass-lined) material or the like. Further, it is efficient for large-scale charging of the sulfuryl fluoride into the pressure-proof reaction vessel to develop a negative pressure atmosphere in the reaction vessel, and then, introduce the sulfuryl fluoride in gas or liquid form under vacuum while increasing the pressure.

The reaction time is generally 72 hours or less. As the reaction time depends on the combination of the raw substrate material and the tertiary amine of carbon number 7 to 18 and the adopted reaction conditions, it is preferable to determine the time at which the raw substrate material has almost disappeared as the end of the reaction while monitoring the progress of the reaction by any analytical means such as gas chromatography, thin-layer chromatography, liquid chromatography or nuclear magnetic resonance.

The target protected optically active fluoroamine of the formula [3] can be obtained by ordinary post treatment of the reaction-terminated liquid. Further, the target compound can be purified to a high chemical purity, as needed, by purification operation such as activated carbon treatment, distillation, recrystallization or column chromatography.

One effective technique of the post treatment is to concentrate the reaction-terminated liquid, dilute the concentration residue with an organic solvent such as toluene or ethyl acetate, wash the residue with an aqueous solution of an inorganic base such as potassium carbonate, further wash the residue with water, and then, concentrate the recovered organic phase. It is possible by such post treatment to obtain the target compound of sufficient quality as the raw substrate material for the hydrolysis reaction of the third step.

Finally, the third step (hydrolysis reaction) will be explained in detail below.

In the third step, the hydrolysis reaction is performed under the acidic condition. More specifically, the hydrolysis reaction can be performed by reacting the protected optically active fluoroamine of the formula [3] with an aqueous solution of an acid catalyst.

Examples of the acid catalyst are: inorganic acids such as hydrogen chloride, hydrogen bromide, hydrogen iodide, sulfuric acid and nitric acid; and organic acids such as formic acid, acetic acid, benzenesulfonic acid and paratoluenesulfonic acid. Among others, inorganic acid are preferred. Particularly preferred are hydrogen chloride and sulfuric acid. It suffices to use the acid catalyst in an amount of 0.1 mol or more per 1 mole of the protected optically active fluoroamine of the formula [3]. The amount of the acid catalyst used is generally preferably in the range of 0.3 to 30 mol, more preferably 0.5 to 20 mol, per 1 mole of the protected optically active fluoroamine of the formula [3].

Further, it suffice to use water in an amount of 1 mol or more per 1 mol of the protected optically active fluoroamine of the formula [3]. The amount of the water used is generally preferably in the range of 3 to 300 mol, more preferably 5 to 150 mol, per 1 mole of the protected optically active fluoroamine of the formula [3].

Examples of the reaction solvent are: aliphatic hydrocarbon solvents such as n-hexane, cyclohexane and n-heptane; aromatic hydrocarbon solvents such as benzene, toluene, ethylbenzene, xylene and mesitylene; ether solvents such as diethyl ether, tetrahydrofuran, diisopropyl ether and tert-butyl methyl ether; and alcohol solvents such as methanol, ethanol, n-propanol and isopropanol; and the like. Among others, n-hexane, n-heptane, toluene, xylene, diisopropyl ether, methanol, ethanol and isopropanol are preferred. Particularly preferred are n-heptane, toluene, xylene and methanol. These reaction solvents can be used alone or in combination thereof. Alternatively, the reaction may be performed in the absence of the reaction solvent or in two-phase reaction system in the third step.

It suffices that the temperature condition ranges from −20 to +150° C. The temperature condition is generally preferably in the range of −10 to +125° C., more preferably 0 to +100° C.

The reaction time is generally 72 hours or less. As the reaction time depends on the combination of the raw substrate material and the acid catalyst and the adopted reaction conditions, it is preferable to determine the time at which the raw substrate material has almost disappeared as the end of the reaction while monitoring the progress of the reaction by any analytical means such as gas chromatography, thin-layer chromatography, liquid chromatography or nuclear magnetic resonance.

The target optically active fluoroamine of the formula [6] can be obtained by ordinary post treatment of the reaction-terminated liquid. Further, the target compound can be purified to a high chemical purity, as needed, by purification operation such as activated carbon treatment, distillation, recrystallization or column chromatography.

In particular, the aldehyde of the formula [5] generated as a by-product can be effectively removed by washing the acidic aqueous solution of the target compound with an organic solvent such as toluene. It is feasible to obtain the same effects as above by a simple operation of performing the reaction in two-phase reaction system using an organic, water-inmiscible solvent such as toluene. The target compound can be obtained with high chemical purity in the form of a salt of the acid catalyst by concentrating the recovered acidic aqueous solution of the target compound, subjecting the concentrated residue to azeotropic dehydration with an organic solvent such as ethyl acetate, and further subjecting the dehydrated residue to hot washing with an organic solvent such as ethyl acetate. In some cases, it may be efficient to recover the target compound in the form of having its amino group protected with a protecting group. As such an amino protecting group, there can be used those described in the above-mentioned reference book.

The thus-obtained salt or protected form of the target compound can be purified to a higher chemical purity by recrystallization etc. Further, the salt or protected form of the target compound can be easily converted to a free base or deprotected form by ordinary deionization (neutralization) or deprotection.

As described above, there is provided according to the present invention the production process of the optically active fluoroamine, including the steps of forming the protected optically active hydroxyamine (imine form, oxazolidine form or mixture thereof) by dehydrative condensation of the optically active hydroxyamine and the aldehyde, reacting the protected optically active hydroxyamine with sulfuryl fluoride ($SO_2F_2$) in the presence of the tertiary amine of carbon number 7 to 18 to thereby convert the protected optically active hydroxyamine to the protected optically active fluoroamine, and then, performing hydrolysis of the protected optically active fluoroamine under the acidic conditions.

The present production process can be industrially easily carried out by the use of the aromatic hydrocarbon group-containing aldehyde and the tertiary amine having a carbon number of 8 to 12 and containing two or more alkyl groups of 3 or more carbon atoms.

Further, there is provided the novel protected optically active fluoroamine as a useful key intermediate for the present production process.

The protected optically active fluoroamine, derived from the aromatic hydrocarbon group-containing aldehyde, serves as a particularly useful key intermediate for easy industrial application of the present production process.

The present invention will be described in more detail below by way of the following examples. It should be noted that these examples are illustrative and are not intended to limit the present invention thereto.

In the following examples, the abbreviations for chemical groups are as follows: Me=methyl; Ph=phenyl; Boc=tert-butoxycarbonyl; i-Pr=isopropyl; and Et=ethyl.

Example 1

To 200 mL of toluene, 30.00 g (399.41 mmol, 1.00 eq, S-configuration, optical purity: 97% ee or higher) of an optically active hydroxyamine of the following formula:

[Chem. 14]

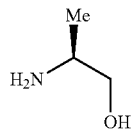

43.60 g (410.86 mmol, 1.03 eq) of an aldehyde of the following formula:

[Chem. 15]

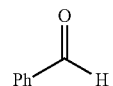

and 0.76 g (4.00 mmol, 0.01 eq) of para-toluenesulfonic acid monohydrate were added. The resulting liquid was stirred for 2 hours at room temperature. The conversion rate of the reaction was determined to be 100% by gas chromatography of the reaction-terminated liquid. The reaction-terminated liquid was vacuum concentrated and vacuum dried, thereby yielding 66.77 g of a 83:17 mixture of an imine-protected optically active hydroxyamine (imine form) of the following formula:

[Chem. 16]

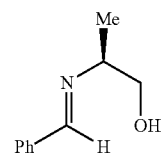

and an oxazolidine-protected optically active hydroxyamine (oxazolidine form, oxazolidine isomer ratio: about 3:2) of the following formula:

[Chem. 17]

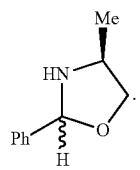

The yield of the reaction product was quantitative (theoretical yield: 65.19 g). The gas chromatographic purity of the reaction product was 98.9%. The $^1$H-NMR measurement results of the reaction product (only the $^1$H-NMR peaks specific to the imine form and to the oxazolidine form) are indicated below.

$^1$H-NMR [reference material: $(CH_3)_4Si$, deuterium solvent: $CDCl_3$] δ ppm/imine: 8.31 (s, 1H), oxazolidine (syn-anti isomer mixture): 5.46, 5.57 (s each, 1H in total; the attributions of these isomer peaks was unidentified).

A pressure-proof reaction vessel of stainless steel (SUS) was charged with 30.00 g (assumed as 179.46 mmol, 1.00 eq) of the mixture of the imine- and oxazolidine-protected optically active hydroxyamines of the above formulas, 120 mL of acetonitrile and 28.51 g (220.60 mmol, 1.23 eq) of diisopropylethylamine, followed by immersing the reaction vessel in a cooling bath of −78° C. and blowing 44.92 g (440.13 mmol, 2.45 eq) of sulfuryl fluoride ($SO_2F_2$) from a cylinder into the reaction vessel. The resulting liquid was stirred for one night at room temperature. The conversion rate of the reaction was determined to be 100% by gas chromatography of the reaction-terminated liquid. The reaction-terminated liquid was vacuum concentrated. The concentration residue was diluted with 100 mL of toluene, washed twice with 50 mL of a saturated aqueous potassium carbonate solution and further washed twice with 50 mL of water. The recovered organic phase was vacuum concentrated and vacuum dried, thereby yielding 29.49 g of a protected optically active fluoroamine of the following formula:

[Chem. 18]

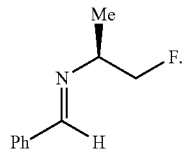

The yield of the reaction product was 99%. The gas chromatographic purity of the recovered organic phase was 92.1%. The $^1$H-NMR and $^{19}$F-NMR measurement results of the reaction product are indicated below.

$^1$H-NMR [reference material: $(CH_3)_4Si$, deuterium solvent: $CDCl_3$] δ ppm/1.26 (d, 6.8 Hz, 3H), 3.70 (m, 1H), 4.46 (dd, 45.9 Hz, 6.8 Hz, 2H), 7.40 (Ar-H, 3H), 7.75 (Ar—H, 2H), 8.34 (s, 1H).

$^{19}$F-NMR [reference material: $C_6F_6$, deuterium solvent: $CDCl_3$] δ ppm/207.22 (dt, 15.0 Hz, 45.9 Hz, 1F).

To 100 mL of methanol, 20.40 g (123.48 mmol, 1.00 eq) of the protected optically active fluoroamine of the above formula and 61.18 g (587.30 mmol, 4.76 eq) of 35% hydrochloric acid were added. The resulting liquid was stirred for one night at room temperature. The conversion rate of the reaction was determined to be 100% by $^{19}$F-NMR of the reaction-terminated liquid. The reaction-terminated liquid was vacuum concentrated. The concentration residue was diluted with 50 mL of water and washed three times with 50 mL of toluene. With this, there was obtained about 75 mL of an aqueous solution containing an optically active fluoroamine hydrochloride salt of the following formula:

[Chem. 19]

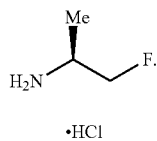

To the whole (assumed as 123.48 mmol, 1.00 eq) of the aqueous solution of the optically active fluoroamine hydrogen chloride salt of the above formula, 100 mL of toluene, 73.44 g (725.76 mmol, 5.88 eq) of triethylamine and 24.00 g (109.97 mmol, 0.89 eq) of $Boc_2O$. The resulting liquid was stirred for one night at room temperature. The conversion rate of the reaction was determined to be 100% by $^{19}$F-NMR of the reaction-terminated liquid. The reaction-terminated liquid was separated into two phases. The recovered organic phase was washed twice with 30 mL of water, vacuum concentrated and vacuum dried, thereby yielding 19.71 g of a Boc-protected optically active fluoroamine (as a crude product) of the following formula:

[Chem. 20]

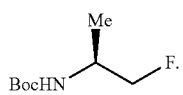

The total yield of the crude product from the protected optically active fluoroamine via the above two reaction steps was 90%. The gas chromatographic purity of the crude product was 94.4%.

The crude product was subjected to solvent displacement treatment by adding 30 mL of n-heptane to the whole (19.71 g) of the crude product and vacuum concentrating the resulting liquid. Then, 12.44 g of a purified product of the Boc-protected optically active fluoroamine was obtained by recrystallization of the crude product from 40 mL of n-heptane. The recovery of the purified product was 63%. The total yield of the purified product from the optically active hydroxyamine via the above four reactions steps (including the recrystallization) was 56%. The gas chromatographic purity of the purified product was 99.4%. The optical purity of the purified product was determined to be 98.6% ee by $^{19}$F-NMR of a Mosher's acid amide of the product (derived after the Boc deprotection). The $^1$H-NMR and $^{19}$F-NMR measurement results of the purified product are indicated below.

$^1$H-NMR [reference material: $(CH_3)_4Si$, deuterium solvent: $CDCl_3$] δ ppm/1.22 (d, 6.8 Hz, 3H), 1.45 (s, 9H), 3.90 (br-d, 1H), 4.33 (ddd, 46.8 Hz, 9.2 Hz, 3.8 Hz, 1H), 4.39 (ddd, 48.0 Hz, 9.2 Hz, 3.8 Hz, 1H), 4.63 (br, 1H).

$^{19}$F-NMR [reference material: $C_6F_6$, deuterium solvent: $CDCl_3$] δ ppm/196.03 (m, 1F).

Example 2

To 130 mL of toluene, 17.50 g (169.64 mmol, 1.00 eq, S-configuration, optical purity: 97% ee or higher) of an optically active hydroxyamine of the following formula:

[Chem. 21]

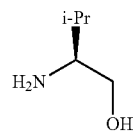

18.60 g (175.27 mmol, 1.03 eq) of an aldehyde of the following formula:

[Chem. 22]

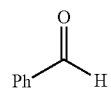

and 0.32 g (1.68 mmol, 0.01 eq) of para-toluenesulfonic acid monohydrate were added. The resulting liquid was stirred for one night at room temperature. The conversion rate of the reaction was determined to be 100% by $^1$H-NMR of the reaction-terminated liquid. The reaction-terminated liquid was vacuum concentrated and vacuum dried, thereby yielding 36.14 g of a 57:43 mixture of an imine-protected optically active hydroxyamine (imine form) of the following formula:

[Chem. 23]

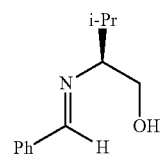

and an oxazolidine-protected optically active hydroxyamine (oxazolidine form, oxazolidine isomer ratio:about 2:1) of the following formula:

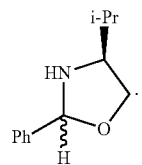

[Chem. 24]

The yield of the reaction product was quantitative (theoretical yield: 32.45 g). The gas chromatographic purity of the reaction product was 96.7%. The $^1$H-NMR measurement results of the reaction product (only the $^1$H-NMR peaks specific to the imine form and the oxazolidine form) are indicated below.

$^1$H-NMR [reference material: $(CH_3)_4Si$, deuterium solvent: $CDCl_3$] δ ppm/imine: 8.29 (s, 1H), oxazolidine (syn-anti isomer mixture): 5.45, 5.48 (s each, 1H in total; the attributions of these isomer peaks was unidentified).

A pressure-proof reaction vessel of stainless steel (SUS) was charged with the whole (assumed as 169.64 mmol, 1.00 eq) of the mixture of the imine- and oxazolidine-protected optically active hydroxyamines of the above formulas, 170 mL of acetonitrile and 87.00 g (673.17 mmol, 3.97 eq) of diisopropylethylamine, followed by immersing the reaction vessel in a cooling bath of −78° C. and blowing 34.58 g (338.82 mmol, 2.00 eq) of sulfuryl fluoride ($SO_2F_2$) from a cylinder into the reaction vessel. The resulting liquid was stirred for one night at room temperature. The conversion rate of the reaction was determined to be 98% by gas chromatography of the reaction-terminated liquid. The reaction-terminated liquid was vacuum concentrated. The concentration residue was diluted with 100 mL of toluene, washed twice with 50 mL of a saturated aqueous potassium carbonate solution and further washed twice with 50 mL of water. The recovered organic phase was vacuum concentrated and vacuum dried, thereby yielding 35.00 g of a protected optically active fluoroamine of the following formula:

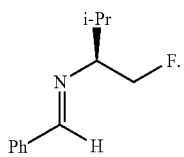

[Chem. 25]

The yield of the reaction product was quantitative (theoretical yield: 32.78 g). The gas chromatographic purity of the reaction product was 93.8%. The $^1$H-NMR and $^{19}$F-NMR measurement results of the reaction product are indicated below.

$^1$H-NMR [reference material: $(CH_3)_4Si$, deuterium solvent: $CDCl_3$] δ ppm/0.94 (d, 6.8 Hz, 3H), 0.97 (d, 6.8 Hz, 3H), 1.98 (m, 1H), 3.20 (m, 1H), 4.54 (dt, 47.2 Hz, 8.6 Hz, 1H), 4.65 (ddd, 47.2 Hz, 8.6 Hz, 3.8 Hz, 1H), 7.42 (Ar—H, 3H), 7.77 (Ar—H, 2H), 8.26 (s, 1H).

$^{19}$F-NMR [reference material: $C_6F_6$, deuterium solvent: $CDCl_3$] δ ppm/202.81 (dt, 15.4 Hz, 47.2 Hz, 1F).

The whole (assumed as 169.64 mmol, 1.00 eq) of the protected optically active fluoroamine of the above formula and 175.82 g (1687.79 mmol, 9.95 eq) of 35% hydrochloric acid were added to 70 mL of toluene. The resulting liquid was stirred for one night at 50° C. The conversion rate of the reaction was determined to be 100% by $^{19}$F-NMR of the reaction-terminated liquid. The reaction-terminated liquid was separated into two phases. The recovered aqueous phase was vacuum concentrated and subjected three times to azeotropic dehydration (vacuum concentration) with 50 mL of ethyl acetate. The thus-obtained residue was washed by stirring with 75 mL of ethyl acetate for 1 hour under reflux, and then, subjected to hot filtration and vacuum drying, thereby yielding 17.99 g of an optically active fluoroamine hydrogen chloride salt of the following formula:

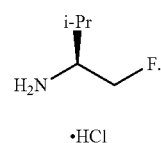

[Chem. 26]

The total yield of the product from the optically active hydroxyamine via the above three reaction steps was 75%. The gas chromatographic purity of a free base of the product was 97.3%. The optical purity of the product was determined to be 99.9% ee by gas chromatography of a Mosher's acid amide of the product (derived after the deionization). The mass spectrum of the free base (by CI method) was 106 (M+1). The $^1$H-NMR and $^{19}$F-NMR measurement results of the product are indicated below.

$^1$H-NMR [reference material: $(CH_3)_4Si$, deuterium solvent: $(CD_3)_2SO$] δ ppm/0.97 (d, 6.8 Hz, 3H), 0.99 (d, 6.8 Hz, 3H), 1.98 (m, 1H), 3.18 (br-d, 1H), 4.64 (ddd, 46.8 Hz, 10.4 Hz, 5.2 Hz, 1H), 4.72 (ddd, 47.2 Hz, 10.4 Hz, 3.2 Hz, 1H), 8.44 (br, 2H). $^{19}$F-NMR [reference material: $C_6F_6$, deuterium solvent: $(CD_3)_2SO$] δ ppm/197.65 (m, 1F).

Comparative Example 1

With reference to Example 1, an imine-protected optically active hydroxyamine (imine form) of the following formula:

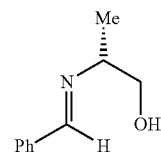

[Chem. 27]

and an oxazolidine-protected optically active hydroxyamine (oxazolidine form) of the following formula:

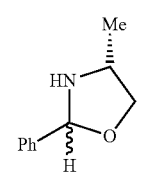

[Chem. 28]

were produced (R-configuration, optical purity: 97% ee or higher, imine-to-oxazolidine ratio: 88:12, oxazolidine isomer ratio: about 3:2).

A pressure-proof reaction vessel of stainless steel (SUS) was charged with 1.000 g (6.127 mmol, 1.00 eq) of the mixture of the imine- and oxazolidine-protected optically active hydroxyamines of the above formulas, 6 mL of acetonitrile and 2.468 g (24.390 mmol, 3.98 eq) of triethylamine, followed by immersing the reaction vessel in a cooling bath of −78° C. and blowing 1.807 g (17.705 mmol, 2.89 eq) of sulfuryl fluoride (SO$_2$F$_2$) from a cylinder into the reaction vessel. The resulting liquid was stirred for one night at room temperature. The conversion rate of the reaction was determined to be 96% by gas chromatography of the reaction-terminated liquid. The reaction-terminated liquid was diluted with 20 mL of ethyl acetate, washed with 10 mL of a saturated aqueous potassium carbonate solution and further washed three times with 10 mL of water. The recovered organic phase was vacuum concentrated and vacuum dried, thereby yielding 0.813 g of a 24:76 mixture of a protected optically active fluoroamine of the following formula:

[Chem. 29]

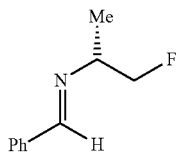

and a quaternary ammonium salt of the following formula:

[Chem. 30]

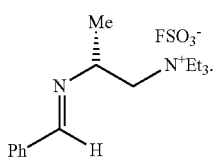

The yield of the product was 44% (protected optically active fluoroamine: 11%, quaternary ammonium salt: 33%). The $^1$H-NMR measurement results of the product (only the $^1$H-NMR peaks specific to the protected optically active fluoroamine and to the quaternary ammonium salt) are indicated below.

$^1$H-NMR [reference material: (CH$_3$)$_4$Si, deuterium solvent: CDCl$_3$] δ ppm/protected optically active fluoroamine: 8.34 (s, 1H), quaternary ammonium salt: 8.49 (s, 1H).

It is seen from the above results that: the target compound was produced, but the product yield remained low, in Comparative Example 1 using triethylamine i.e. tertiary amine of carbon number less than 7; whereas the target protected optically active fluoroamine was produced with much higher yield in the production process of the present invention (Examples).

The invention claimed is:

1. A process for producing a protected optically active fluoroamine of the formula [3], comprising:
    reacting an imine-protected optically active hydroxyamine of the formula [1], an oxazolidine-protected optically active hydroxyamine of the formula [2] or a mixture thereof with sulfuryl fluoride (SO$_2$F$_2$) in the presence of a tertiary amine in which all of three ammonia hydrogen atoms have been replaced by alkyl groups and which has a carbon number of 7 to 18

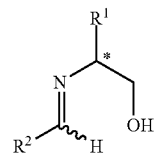

[1]

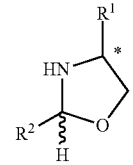

[2]

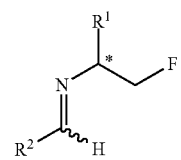

[3]

where R$^1$ and R$^2$ each independently represent an alkyl group or an aromatic ring group; * represents an asymmetric carbon; the stereochemistry of the asymmetric carbon is maintained through the reacting; and the wavy line indicates in the formula (1) and in the formula (3) that the nitrogen-carbon group is in an E-configuration, a Z-configuration or a mixture thereof and indicates in the formula (2) that the substituent group R$^1$ is in a syn-configuration, an anti-configuration or a mixture thereof.

2. The process for producing the protected optically active fluoroamine according to claim 1, wherein R$^2$ of the imine-protected optically active hydroxyamine of the formula [1] or the oxazolidine-protected optically active hydoxyamine of the formula [2] is an aromatic hydrocarbon group; and the tertiary amine has a carbon number of 8 to 12 and contains two or more alkyl groups of 3 or more carbon atoms.

3. The process for producing the protected optically active fluoroamine according to claim 1, comprising forming the imine-protected optically active hydroxyamine of the formula [1] or the oxazolidine-protected optically active hydroxyamine of the formula [2] by dehydrative condensation of an optically active hydroxyamine of the formula [4] and an aldehyde of the formula [5]

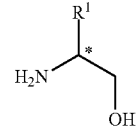

[4]

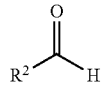

[5]

where R$^1$ and R$^2$ each independently represent an alkyl group or an aromatic ring group; and
    * represents an asymmetric carbon of which the stereochemistry is maintained through the dehydrative condensation.

4. The process for producing the protected optically active fluoroamine according to claim 3, wherein R$^1$ is an alkyl group having 1 to 9 carbon atoms in the formula [4].

5. The process for producing the protected optically active fluoroamine according to claim 3, wherein the dehydrative condensation is preformed in the presence of an acid catalyst.

6. The process for producing the protected optically active fluoroamine according to claim 5, wherein the acid catalyst is either para-toluenesulfonic acid or pyridinium para-toluenesulfonate.

7. The process for producing the protected optically active fluoroamine according to claim 1, wherein the tertiary amine is diisopropylethylamine.

8. A process for producing an optically active fluoroamine of the formula [6], comprising: performing, under acidic conditions, hydrolysis of the protected optically active fluoroamine of the formula [3] produced by the process according to claim 1

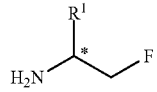

[6]

where $R^1$ represents an alkyl group or an aromatic ring group; and * represents an asymmetric carbon of which the stereochemistry is maintained through the hydrolysis.

9. The process for producing the optically active fluoroamine according to claim 8, wherein the hydrolysis is performed by reacting the protected optically active fluoroamine of the formula [3] with an aqueous solution of an acid catalyst; and the acid catalyst is either hydrogen chloride or sulfuric acid.

* * * * *